(12) United States Patent
Mechoulam et al.

(10) Patent No.: US 11,324,709 B2
(45) Date of Patent: May 10, 2022

(54) FATTY ACID AMIDES AND USES THEREOF IN THE TREATMENT OF ADDICTION DISORDER AND ADDICTION RELATED CONDITIONS

(71) Applicants: Yissum Research Development Company of The Hebrew University of Jerusalem Ltd., Jerusalem (IL); VIRGINIA COMMONWEALTH UNIVERSITY, Richmond, VA (US); UNIVERSITY OF GUELPH, Guelph (CA)

(72) Inventors: Raphael Mechoulam, Jerusalem (IL); Vincenzo Di Marzo, Naples (IT); Fabiana Piscitelli, Mondragone (IT); Aron H. Lichtman, Henrico, VA (US); Imad M. Damaj, North Chesterfield, VA (US); Linda Parker, Campbell River (CA); Rami Yaka, Kfar Uria (IL)

(73) Assignee: Yissum Research Development Company of The Hebrew University of Jerusalem Ltd., Jerusalem (IL)

( * ) Notice: Subject to any disclaimer, the term of this patent is extended or adjusted under 35 U.S.C. 154(b) by 13 days.

(21) Appl. No.: 16/613,213

(22) PCT Filed: May 22, 2018

(86) PCT No.: PCT/IL2018/050552
§ 371 (c)(1),
(2) Date: Nov. 13, 2019

(87) PCT Pub. No.: WO2018/216008
PCT Pub. Date: Nov. 29, 2018

(65) Prior Publication Data
US 2020/0108037 A1 Apr. 9, 2020

Related U.S. Application Data

(60) Provisional application No. 62/509,252, filed on May 22, 2017.

(51) Int. Cl.
*A61K 31/20* (2006.01)
*A61P 25/34* (2006.01)
*A61P 25/36* (2006.01)
*A61P 25/32* (2006.01)

(52) U.S. Cl.
CPC .............. *A61K 31/20* (2013.01); *A61P 25/32* (2018.01); *A61P 25/34* (2018.01); *A61P 25/36* (2018.01)

(58) Field of Classification Search
CPC .......... A61K 31/20; A61P 25/34; A61P 25/36; A61P 25/32
See application file for complete search history.

(56) References Cited

U.S. PATENT DOCUMENTS

2010/0026623 A1  10/2010  Jackson et al.

FOREIGN PATENT DOCUMENTS

| EP | 0 432 039 A2 | 6/1991 |
| WO | WO 2003/006007 | * 1/2003 |
| WO | WO 2003/006007 A1 | 1/2003 |

OTHER PUBLICATIONS

Farrell (Biosynthesis of Fatty Acid Amimde-Thesis 2010).*
Barbara, G. et al. (2009). T-type calcium channel inhibition underlies the analgesic effects of the endogenous lipoamino acids. Journal of Neuroscience, 29(42), 13106-13114.
Beiser et al. (2017). Chronic treatment with Tempol during acquisition or withdrawal from CPP abolishes the expression of cocaine reward and diminishes oxidative damage. Scientific reports, 7(1), 1-9.
Boudreau, A. C. et al. (2005). Behavioral sensitization to cocaine is associated with increased AMPA receptor surface expression in the nucleus accumbens. Journal of Neuroscience, 25(40), 9144-9151.
Eisenberg, R. M. (1982). Further studies on the acute dependence produced by morphine in opiate naive rats. Life sciences, 31(15), 1531-1540.
Heishman, S. J. et al. (1990). Acute opioid physical dependence in humans: effect of naloxone at 6 and 24 hours postmorphine. Pharmacology Biochemistry and Behavior, 36(2), 393-399.
International Search Report issued for PCT Application No. PCT/IL2018/050552 dated Oct. 9, 2018.
June, H. L. et al. (1995). Acute physical dependence: time course and relation to human plasma morphine concentrations. Clinical Pharmacology & Therapeutics, 57(3), 270-280.
Martin, W. R. et al. (1964). A comparison between acute and chronic physical dependence in the chronic spinal dog. Journal of Pharmacology and Experimental Therapeutics, 146(3), 385-394.
Naqvi, N. H. et al. (2007). Damage to the insula disrupts addiction to cigarette smoking. Science, 315(5811), 531-534.
Naqvi, N. H. et al. (2014). The insula: a critical neural substrate for craving and drug seeking under conflict and risk. Annals of the New York Academy of Sciences, 1316, 53.
Parker, L. A. et al. (1998). Naloxone-precipitated morphine withdrawal induced place aversions: effect of naloxone at 24 hours postmorphine. Pharmacology Biochemistry and Behavior, 61(3), 331-333.
Parker, L. A. et al. (2002). The aversive properties of acute morphine dependence persist 48 h after a single exposure to morphine: evaluation by taste and place conditioning. Pharmacology and Behavior, 72(1-2), 87-92.

(Continued)

*Primary Examiner* — Shirley V Gembeh
(74) *Attorney, Agent, or Firm* — Mark S. Cohen; Pearl Cohen Zedek Latzer Baratz LLP

(57) ABSTRACT

The present invention is directed to a fatty acid amide of an amino acid, including a stereoisomer and a salt thereof for use in the treatment of a patient suffering from any type of addiction disorder, substance abuse disorder, including any condition and symptom associated therewith and including withdrawal syndrome and relapse addiction during and after a rehabilitation treatment of said patient.

12 Claims, 10 Drawing Sheets

(56) References Cited

OTHER PUBLICATIONS

Schumann, J. et al. (2009). Prolonged withdrawal from repeated noncontingent cocaine exposure increases NMDA receptor expression and ERK activity in the nucleus accumbens. Journal of Neuroscience, 29(21), 6955-6963.

Wu, J., et al. (2017). N-oleoylglycine-induced hyperphagia is associated with the activation of agouti-related protein (AgRP) neuron by cannabinoid receptor type 1 (CB1R). Journal of agricultural and food chemistry, 65(5), 1051-1057.

Yehuda, S. (2002). Possible anti-Parkinson properties of N-($\alpha$-linolenoyl) tyrosine: a new molecule. Pharmacology Biochemistry and Behavior, 72(1-2), 7-11.

\* cited by examiner

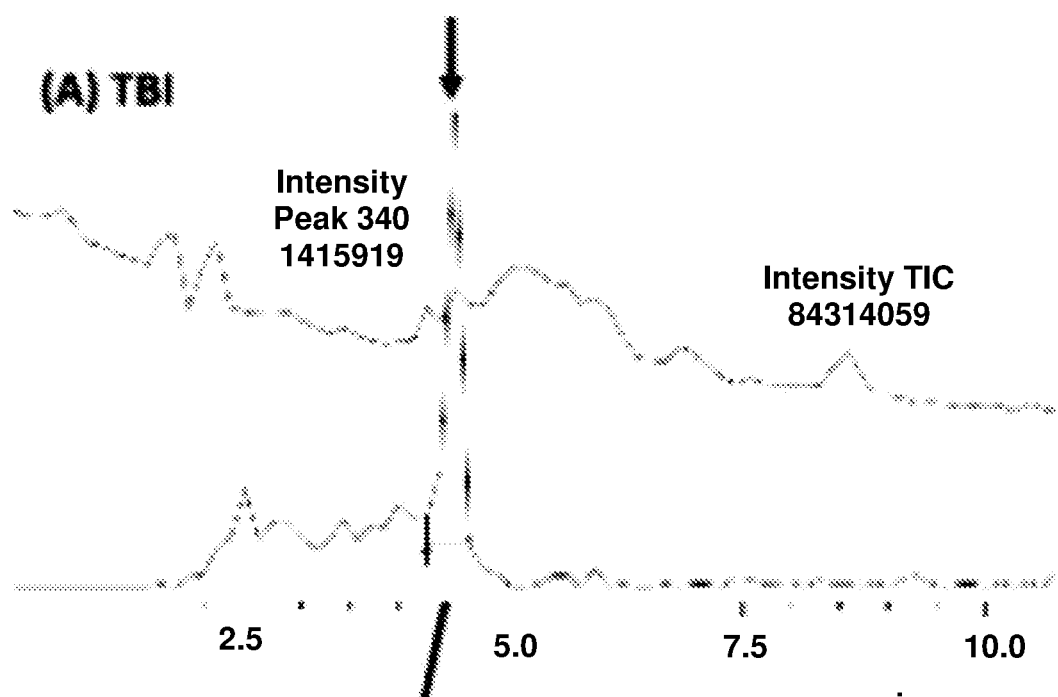
Figure 3A(1)

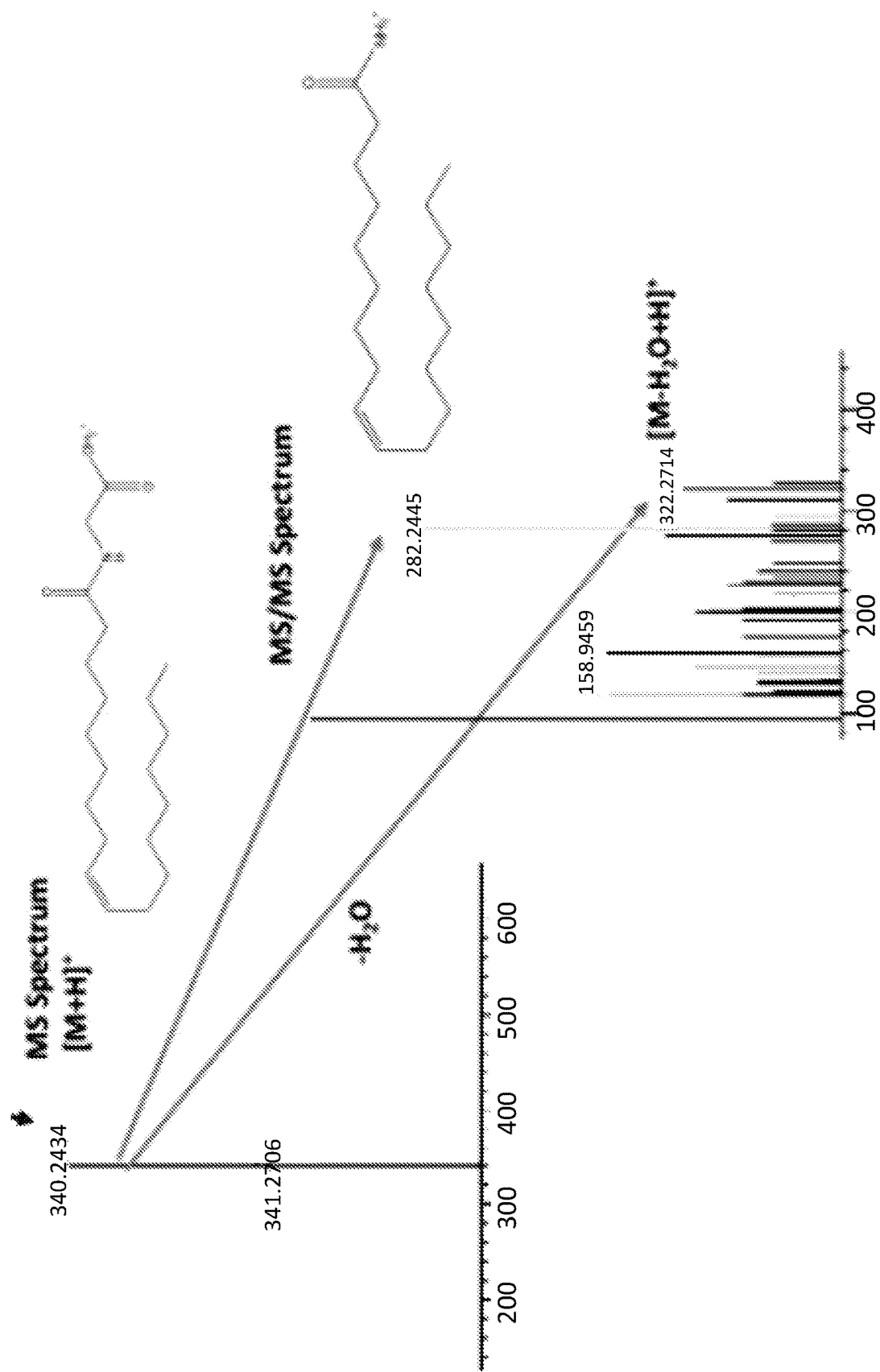
Figure 3A(2)
Figure 3A(3)

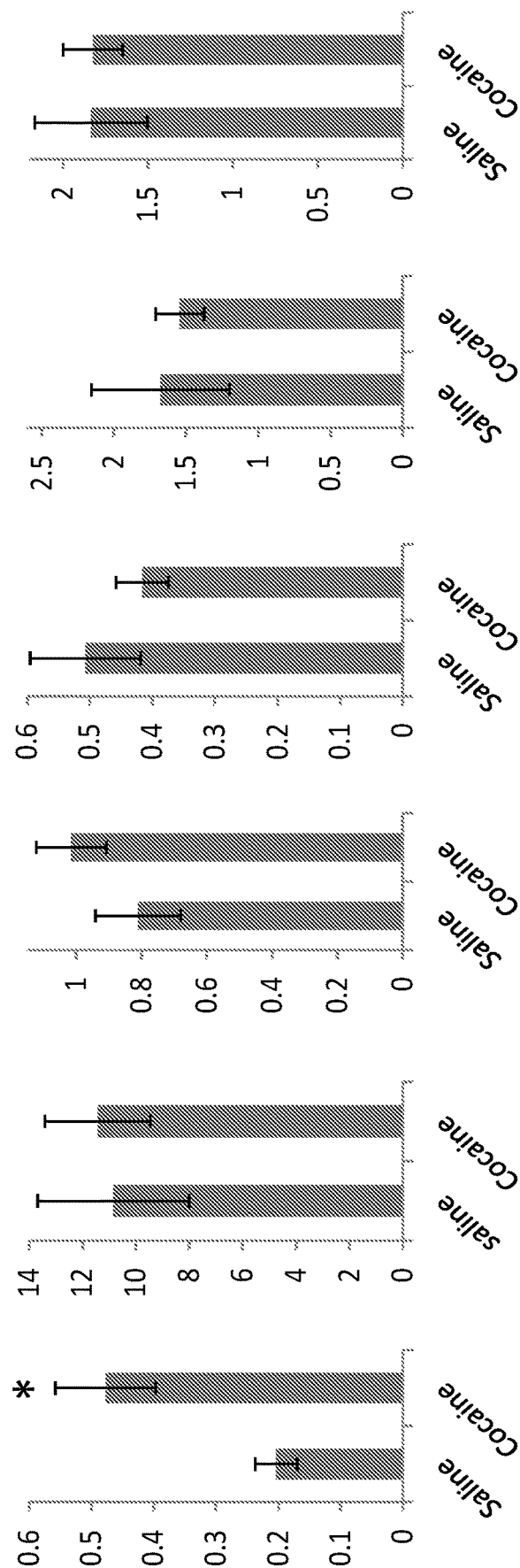

FATTY ACID AMIDES AND USES THEREOF IN THE TREATMENT OF ADDICTION DISORDER AND ADDICTION RELATED CONDITIONS

CROSS-REFERENCE TO RELATED APPLICATIONS

This application is a National Phase Application of PCT International Application No. PCT/IL2018/050552, International Filing Date May 22, 2018, claiming the benefit of U.S. Patent Application No. 62/509,252, filed May 22, 2017 which are hereby incorporated by reference.

BACKGROUND OF THE INVENTION

Cigarette smokers having traumatic brain injury (TBI)-induced damage to the insular cortex display showed cessation of nicotine addiction (Naqvi et al, 2007; Naqvi et al. 2014). Donvito et al. subjected anesthesized mice to the weight drop model of TBI and harvested the insular cortex, hippocampus and hypothalamus 24 hr later. Using targeted lipoomics techniques, they showed profound increases in OlGly in the insular cortex, but not in the hippocampus or hypothalamus of brain damaged mice, not in sham mice. OlGly itself produced neither a place preference nor a place aversion, but it interfered with both a nicotine-induced place preference and reduced precipitated withdrawal responses and a withdrawal induced place aversion in nicotine-dependent mice.

Another drug abuse disorder with considerable cost to society and the individual is opiate addiction. Of the 21.5 million Americans 12 or older that had a substance use disorder in 2014, 1.9 million had a substance use disorder involving prescription pain relievers and 586,000 had a substance use disorder involving heroin (National Institute on Drug Abuse 2015). Withdrawal from opiates is a driving force in the maintenance of opiate addiction (eg, Koob, 2009a,b). Morphine withdrawal (MWD) can be produced by terminating chronic exposure to morphine or by administering an opiate antagonist to morphine pretreated animals. Even after a single exposure to a high dose of morphine, administration of naloxone several hours later produces withdrawal symptoms in humans (Heishman et al, 1990; June et al, 1995) and other animals (Eisenberg, 1982; Martin and Eades, 1964). The withdrawal is apparent not only by behavioral symptoms of abstinence, but also by the ability of such withdrawal to serve as an aversive motivational stimulus. Parker et al. (Parker & Joshi, 1998; Parker et al., 2002) demonstrated that the aversive properties of naloxone precipitated MWD were evident up to 48 hr. after a single injection of morphine, but not saline, in a conditioned place aversion (CPA) paradigm.

SUMMARY OF THE INVENTION

The present invention thus provides a fatty acid amide of an amino acid, including a stereoisomer and a salt thereof for use in the treatment of a patient suffering from an addiction disorder including any condition and symptom associated therewith.

The present invention thus provides a fatty acid amide of an amino acid, including a stereoisomer and a salt thereof for use in the treatment of substance abuse disorder, including conditions and symptoms associated therewith.

In a further aspect the invention provides a fatty acid amide of an amino acid, including a stereoisomer and a salt thereof for use in the treatment of a patient suffering from an addiction to a substance including any disorder, condition and symptom associated therewith.

The term "addiction" or "addiction disorder" should be understood to include a primary, chronic disease of brain reward, motivation, memory and related circuitry. The term refers both to stimuli/compulsive seeking behaviors and to substance abuse dependency. The terms "addiction to a substance" and/or "substance abuse disorder" and/or "substance dependence disorder" and/or "dependence to a substance" fall under the general addiction disorder and relate specifically to the dependency of a subject to a particular substance or substances that amount to an addiction disorder as defined hereinabove.

Compulsive seeking behaviors include, but are not limited to gambling, sex addiction, shopping addiction, addiction to compulsive behaviors (such as excessive cleaning and other compulsive behaviors generally in the OCD spectrum) and any combinations thereof.

Substance abuse addictions include but are not limited to drug addiction (including but not limited to opiates, such as heroin or other morphine derivatives, cocaine, amphetamines, cannabis, addictive drugs of any type including but not limited to sleep inducing agent, pain relieving agents, anti-histaminic agents and so forth), cigarette smoking, alcohol consumption, food consumption and any combinations thereto.

Without being bound by theory, addiction affects neurotransmission and interactions within reward structures of the brain, including the nucleus accumbens, anterior cingulate cortex, basal forebrain and amygdala, such that motivational hierarchies are altered and addictive behaviors, which may or may not include alcohol and other drug use, supplant healthy, self-care related behaviors. Addiction also affects neurotransmission and interactions between cortical and hippocampal circuits and brain reward structures, such that the memory of previous exposures to rewards (such as food, sex, alcohol and other drugs) leads to a biological and behavioral response to external cues, in turn triggering craving and/or engagement in addictive behaviors.

Addiction is characterized by the inability to consistently abstain from a substance or behavioral patterns, impaired behavioral control, craving for substance or rewarding experience/behavior, diminished recognition of significant problems with subject's behavior and interpersonal relationship; and dysfunctional emotional response. The power of external cues to trigger craving and drug use, as well as to increase the frequency of engagement in other potentially addictive behaviors, is also a characteristic of addiction, with the hippocampus being important in memory of previous euphoric or dysphoric experiences, and with the amygdala being important in having motivation concentrate on selecting behaviors associated with these past experiences.

Persistent risk and/or recurrence of relapse, after periods of abstinence, is another fundamental feature of addiction. This can be triggered by exposure to rewarding substances and behaviors, by exposure to environmental cues to use, and by exposure to emotional stressors that trigger heightened activity in brain stress circuits.

Some of the symptoms associated with addiction include for example, impairment in executive functioning, problems with perception, learning, impulse control, compulsivity, and judgment, lower readiness to change their dysfunctional behaviors, display an apparent lack of appreciation of the magnitude of cumulative problems and complications. Additional symptoms include aspects of a person's behaviors, cognitions, emotions, and interactions with others, including a person's ability to relate to members of their family, to members of their community, to their own psychological state, and to things that transcend their daily experience.

Behavioral manifestations and complications associated with addiction, primarily due to impaired control, can include: excessive use and/or engagement in addictive behaviors, at higher frequencies and/or quantities than the person intended, often associated with a persistent desire for and unsuccessful attempts at behavioral control, excessive time lost in substance use or recovering from the effects of substance use and/or engagement in addictive behaviors, with significant adverse impact on social and occupational functioning (e.g. the development of interpersonal relationship problems or the neglect of responsibilities at home, school or work), continued use and/or engagement in addictive behaviors, despite the presence of persistent or recurrent physical or psychological problems which may have been caused or exacerbated by substance use and/or related addictive behaviors, narrowing of the behavioral repertoire focusing on rewards that are part of addiction; and an apparent lack of ability and/or readiness to take consistent, ameliorative action despite recognition of problems.

Cognitive symptoms associated with addiction can include: preoccupation with substance use; altered evaluations of the relative benefits and detriments associated with drugs or rewarding behaviors; and the inaccurate belief that problems experienced in one's life are attributable to other causes rather than being a predictable consequence of addiction.

Emotional symptoms associated with addiction include: increased anxiety, dysphoria and emotional pain; increased sensitivity to stressors associated with the recruitment of brain stress systems, such that "things seem more stressful" as a result; and difficulty in identifying feelings, distinguishing between feelings and the bodily sensations of emotional arousal, and describing feelings to other people (sometimes referred to as alexithymia).

As addiction is a chronic disease, periods of relapse, which may interrupt spans of remission, are a common feature of addiction. It is also important to recognize that return to drug use or pathological pursuit of rewards is not inevitable.

The qualitative ways in which the brain and behavior respond to drug exposure and engagement in addictive behaviors are different at later stages of addiction than in earlier stages, indicating progression, which may not be overtly apparent.

The invention further provides a method of treating addiction disorder including any condition and symptom associated therewith in a patient suffering therefrom, said method comprising administering to said patient a fatty acid amide of an amino acid, including a stereoisomer and a salt thereof.

In a further aspect the invention provides a method of treating substance abuse disorder, including conditions and symptoms associated therewith in a patient suffering therefrom, said method comprising administering to said patient a fatty acid amide of an amino acid, including a stereoisomer and a salt thereof.

In yet another aspect the invention provides a method of treating addiction to a substance including any disorder, condition and symptom associated therewith in a patient suffering therefrom, said method comprising administering to said patient a fatty acid amide of an amino acid, including a stereoisomer and a salt thereof.

In some embodiments, said substance is a drug (including stimulants like cocaine and heroin, barbiturates, nicotine, pain relieving drugs, sleep induced drugs), a cigarette, alcoholic beverage, food and any combinations thereof.

In some embodiments, said addiction is drug addiction (including pain relieving drugs, opioids, sleep inducing drugs and so forth), cigarette addiction (also nicotine addiction), alcohol addiction, food addiction, behavioral addiction (including OCD behavior of any sort, sex addiction, narcolepsy and so forth) and any combinations thereof.

In some embodiments, said addiction is nicotine addiction. In other embodiments, said addiction is opioid addiction (substances that act on opioid receptors producing morphine-like effects).

In some embodiments, said substance is a drug, a cigarette, alcoholic beverage, food and any combinations thereof. In further embodiments, said substance is nicotine. In other embodiments, said substance is an opioid.

The term "treatment of addiction" as used herein refers to the administering of a therapeutic amount of a compound and/or a composition disclosed herein which is effective to ameliorate the addictive disorder, including its undesired symptoms and conditions associated therewith, to prevent the manifestation of the addictive disorder including its symptoms and conditions before they occur (for example in subjects in need of a therapeutic regime of a medicament that has an addictive potential, such as before or during treatment with opioids), to slow down the progression of the addiction, slow down the deterioration of the addiction and its symptoms, to enhance the onset of remission period, slow down the irreversible damage caused in the progressive chronic stage of the addiction, to delay the onset of said progressive stage, to lessen the severity or cure the addiction and addictive behavior, to improve recovery, or to prevent the addiction form occurring, to decrease the frequency and intensity of addiction relapse, to sustain periods of remission from addiction and addictive behavior, to optimize the subject's level of functioning during periods of remission; and any combination of the above.

The invention further provides a fatty acid amide of an amino acid, including a stereoisomer and a salt thereof for use in the treatment of a patient suffering from withdrawal syndrome during a rehabilitation or detoxification from abusive substance addiction treatment.

When referring to "withdrawal syndrome during a rehabilitation or detoxification from abusive substance addiction treatment" should be understood to relate to any symptoms occurring to a patient going through rehabilitation or detoxification treatment during which there is a full or partial discontinuation usage or said abusive substance or dosage reduction of said abusive substance.

In another aspect the invention provides a fatty acid amide of an amino acid, including a stereoisomer and a salt thereof for use in the treatment of a patient suffering from relapse addiction during or after rehabilitation or detoxification from abusive substance addiction treatment.

When referring to "relapse addiction during or after rehabilitation or detoxification from abusive substance addiction treatment" should be understood to relate to the outcome of transgression during or after a rehabilitation or detoxification from abusive substance addiction treatment.

In some embodiments, said addiction is nicotine addiction. In other embodiments, aid addiction is opioid addiction. In other embodiments, said addiction is drug addiction. In further embodiments, said addiction is pain killer drug addiction (including addiction to analgesic drugs, addiction to drugs used to reduce pain, also known as analgesic drug addiction). In further embodiments, said addiction is analgesic drug addiction. In other embodiments, said addiction is cocaine addiction. In further embodiments, said addiction is behavioral addiction (including but not limited to: addiction to eating, addiction to drinking, vomiting, sex, shopping, gaming, obsessive compulsive behaviors, gambling, and so forth).

In some embodiments, said substance is selected from a drug, a cigarette, alcoholic beverage, food and any combinations thereof. In some embodiments, said substance is nicotine. In other embodiments, said substance is an opioid. In further embodiments, said substance is cocaine. In further embodiments, said substance is alcohol. In further embodiments, said substance is food. In further embodiments, said substance is pain killer drug.

The invention further provides a method of treating a patient suffering from withdrawal syndrome during a rehabilitation or detoxification from abusive substance addiction treatment, said method comprising administering to said patient a fatty acid amide of an amino acid, including a stereoisomer and a salt thereof.

The invention further covers a method of treating a patient suffering from relapse addiction during or after rehabilitation or detoxification from abusive substance addiction treatment, said method comprising administering to said patient a fatty acid amide of an amino acid, including a stereoisomer and a salt thereof.

As used herein the term "fatty acid amide of an amino acid" is meant to encompass a compound achieved by the conjugation of a fatty acid moiety (having the general formula $—C(=O)R_1$, wherein $R_1$ is as defined herein) and an amino acid moiety (having the general formula $—NHCR_2R_3C(=O)OH$, wherein $R_2$ and $R_3$ are as defined herein) through the formation of an amidic bond between the nitrogen atom of the amino acid moiety ($—NHCR_2R_3C(=O)OH$) and the carbonylic atom ($—C(=O)R_1$) of the fatty acid moiety. It should be understood that while compounds of the invention are generally referred to as a conjugate of a fatty acid moiety and an amino acid moiety, the conjugate of the invention may be formed from a variety of precursors, employing a single or multi-step synthetic methodologies.

When referring to a "fatty acid moiety" it should be understood to encompass an acyl moiety derivable from a fatty acid, namely being generally of the form $R_1C(=O)—$, wherein $R_1$ represents the aliphatic chain (saturated or unsaturated) of the corresponding fatty acid, and wherein the point of attachment of the fatty acid moiety to the amino acid moiety of the fatty acid amide is through the carbonyl carbon atom of the fatty acid moiety.

As used herein the term "fatty acid" is meant to encompass a mono carboxylic acid having an aliphatic chain ("tail"), wherein said aliphatic chain may be either saturated, mono-unsaturated (having one unsaturated bond anywhere on the aliphatic chain) or poly unsaturated (having at least two unsaturated bonds anywhere on the aliphatic chain). An unsaturated bond on the aliphatic chain may be a double (in the cis and/or trans configuration) or a triple bond. The length of the aliphatic chain (being either saturated, mono-unsaturated or polyunsaturated) of a fatty acid may vary between 10 to 30 or in some embodiments between 13 to 22 carbon atoms. Fatty acids may be derived from a natural source (either an animal or plant source), synthetic source or semi-synthetic source.

Non-limiting examples of saturated fatty acids are lauric acid, myristic acid, palmitic acid and stearic acid. Non-limiting examples of monounsaturated fatty acids are myristoleic acid, palmitoleic acid and oleic acid. Non-limiting examples of polyunsaturated fatty acids are linoleic acid, α-linolenic acid, arachidonic acid, eicosapentaenoic acid, erucic acid and docosahexaenoic acid.

In some embodiments, said fatty acid moiety of a fatty acid amide is selected from a saturated fatty acid moiety (i.e. $R_1$ is a hydrocarbon that consists only of single saturated bonds), a mono-unsaturated fatty acid moiety (i.e. $R_1$ is a hydrocarbon that comprises one unsaturated bond—either a double or triple bond) and a poly unsaturated fatty acid moiety (i.e. $R_1$ is a hydrocarbon that comprises at least two unsaturated bond—each independently either a double or triple bond). In other embodiments of the invention, the fatty acid moiety is an oleoyl fatty acid moiety ($CH_3(CH_2)_7CH=CH(CH_2)_7C(=O)—$), namely derived from the corresponding oleic acid.

In some further embodiments, said fatty acid moiety is substituted by at least one group selected from $—C_1-C_6$ alkyl, $—OH$, $—OR'$, $—SH$ and $—SR"$, wherein $R'$ and $R"$ are each independently straight or branched $—C_1-C_6$ alkyl. In other embodiments, said fatty acid moiety is substituted by at least one straight or branched $—C_1-C_6$ alkyl. In other embodiments, said fatty acid moiety is substituted by at least two straight or branched $—C_1-C_6$ alkyl. In yet other embodiments, said at least one $C_1-C_6$ alkyl is methyl.

In further embodiments, said at least one substitution is on at least one of the α- or β-positions of said fatty acid moiety. As known in the art, the "α-position of said fatty acid moiety" is the carbon atom on the aliphatic chain of the fatty acid moiety which is directly adjacent to the carbonyl carbon atom of the fatty acid moiety; the "β-position of said fatty acid moiety" is the carbon atom on the aliphatic chain of the fatty acid moiety which is the second carbon atom adjacent to the carbonyl carbon atom of the fatty acid moiety.

In some embodiments, a fatty acid amide of the invention is substituted at the α-position of the fatty acid moiety. In other embodiments, a fatty acid amide of the invention is substituted at the β-position of the fatty acid moiety. In further embodiments, a fatty acid amide of the invention is substituted at both the α- and β-positions of the fatty acid moiety.

When referring to an "amino acid moiety" it should be understood to encompass a radical derivable from an amino acid, namely being generally of the formula $—NHCR_2R_3COOH$, wherein the point of attachment of said amino acid moiety to a fatty acid moiety, as defined herein, is through the amine of the amino acid moiety, as explained above.

The "amino acid" is an amino acid (i.e., alpha-amino acid or beta-amino acid) as known in the art. In some embodiments, the amino acid moiety is derived from an amino acid of the general formula $H_2NCR_2R_3COOH$, wherein $R_2$ and $R_3$ are as defined above. Non-limiting examples of amino acids which correspond to the amino acid moiety of a compound defined herein are alanine, asparagine, aspartate, cysteine, glutamate, glutamine, glycine, dimethylglycine, proline, serine, tyrosine, arginine, histidine, isoleucine, leucine, lysine, methionine, phenylalanine, threonine, tryptophan, and valine. An amino acid as used herein may be derived from of a natural source, synthetic or semi-synthetic source. An amino acid as used herein may also be in the D- or L-configuration. In some embodiments, an amino acid is an L-amino acid.

In some embodiments, said amino acid moiety is selected from serine, glycine, dimethylglycine, alanine, cysteine, tyrosine and phenylalanine. In other embodiments, said amino acid moiety is serine.

In some embodiments, of the invention said fatty acid moiety is optionally substituted by one group selected from —$C_1$-$C_6$ alkyl, —OH, —O($C_1$-$C_{10}$ alkyl), —SH and —S($C_1$-$C_{10}$ alkyl); and the amino acid moiety is optionally substituted by one group selected from —$C_1$-$C_6$ alkyl, —OH and —O($C_1$-$C_{10}$ alkyl), phenyl and phenol.

In further embodiments, said amino acid moiety is unsubstituted.

In still further embodiments, said amino acid moiety is substituted by at least one group selected from —$C_1$-$C_6$ alkyl, —OH, and —O($C_1$-$C_{10}$ alkyl), wherein $R_3$ is —$C_1$-$C_6$ alkyl. In other embodiments, said amino acid is substituted by at least one —$C_1$-$C_6$ alkyl. In other embodiments, said amino acid is substituted by at least two —$C_1$-$C_6$ alkyl. In further embodiments, said —$C_1$-$C_6$ alkyl is methyl. In yet additional embodiments, said substitution is on the α-position of said amino acid moiety.

The "α-position of said amino acid moiety" is the carbon atom on the amino acid moiety which is directly adjacent to the carbonyl carbon atom of the amino acid moiety.

In some further embodiments, said amino acid moiety is selected from a moiety of serine, cysteine, glycine, dimethylglycine, alanine, tyrosine and phenylalanine. In some embodiments, said amino acid moiety is substituted by at least one group selected from straight or branched —$C_1$-$C_6$ alkyl, straight or branched —$C_2$-$C_6$ alkenyl, straight or branched —$C_2$-$C_6$ alkynyl, —OH, and —O($C_1$-$C_{10}$ alkyl).

In some other embodiments, said amino acid is substituted by at least one —$C_1$-$C_6$ alkyl. In other embodiments, said amino acid is substituted by at least two —$C_1$-$C_6$ alkyl. In yet further embodiments, said —$C_1$-$C_6$ alkyl is methyl. In some embodiments, said substitution is on the α-position of said amino acid moiety.

In some embodiments, said fatty acid moiety is substituted by at least one group selected from —$C_1$-$C_6$ alkyl, —OH, —O($C_1$-$C_{10}$ alkyl), —SH and —S($C_1$-$C_{10}$ alkyl). In further embodiments, said fatty acid moiety is substituted by at least one —$C_1$-$C_6$ alkyl. In some embodiments, at least one $C_1$-$C_6$ alkyl is methyl. In further embodiments, said at least one substitution is on at least one of α- or β-positions of said fatty acid moiety.

In some embodiments, a fatty acid amide of the invention is a compound of general formula (I), including a stereoisomer and a salt thereof:

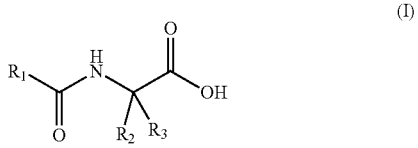

(I)

Wherein $R_1$ is selected from straight or branched —$C_{13}$-$C_{22}$ alkyl, straight or branched —$C_{13}$-$C_{22}$ alkenyl and straight or branched —$C_{13}$-$C_{22}$ alkynyl; optionally substituted by at least one group selected from —$C_1$-$C_6$ alkyl, —OH, —O($C_1$-$C_{10}$ alkyl), —SH and —S($C_1$-$C_{10}$ alkyl); $R_2$ and $R_3$ are independently selected from H, straight or branched —$C_1$-$C_6$ alkyl, straight or branched —$C_2$-$C_6$ alkenyl, straight or branched —$C_2$-$C_6$ alkynyl; each optionally substituted by at least one —OH, —SH, —O($C_1$-$C_6$ alkyl), phenyl and phenol; provided that at least one of $R_2$ and $R_3$ is different than H.

In some embodiments, $R_2$ is straight or branched —$C_1$-$C_6$ alkyl. In other embodiments, $R_3$ is straight or branched —$C_1$-$C_6$ alkyl. In further embodiments, $R_2$ and $R_3$ are each independently —$C_1$-$C_6$ alkyl. In yet other embodiments, said —$C_1$-$C_6$ alkyl is methyl. In some embodiments, $R_1$ is a straight or branched —$C_{13}$-$C_{22}$ alkenyl. In some embodiments, said straight or branched —$C_{13}$-$C_{22}$ alkenyl comprises between 1 to 6 double bonds.

The term "stereoisomer" as used herein is meant to encompass an isomer that possess identical constitution as a corresponding stereoisomer, but which differs in the arrangement of its atoms in space from the corresponding stereoisomer. For example, stereoisomers may be enantiomers, diastereomers and/or cis-trans (E/Z) isomers. It should be understood that a composition comprising a fatty acid amide of the invention may comprise single enantiomers, single diastereomers as well as mixtures thereof at any ratio (for example racemic mixtures, non-racemic mixtures, mixtures of at least two diastereomers and so forth). Furthermore, the invention encompasses any stereoisomer of a fatty acid amide of the invention achieved through in vivo or in vitro metabolism, or by any type of synthetic rout.

The term "salt" as used herein is meant to encompass any salt achieved by acid or base addition. In some embodiments, the salt is an acid addition salt obtained by protonation of a fatty acid amide of the invention (for example at the amidic moiety). In other embodiments, the salt is a base addition salt obtained by deprotonation of a proton from the fatty acid amide of the invention (for example from the acidic moiety, i.e. —COOH of the fatty acid amide). Counter ion forming a salt of a fatty acid amide of the invention can, in a non-limiting fashion, include inorganic or organic cations, which in some embodiments are pharmaceutically acceptable, such as alkaline metal cations e.g. potassium or sodium cation, alkaline earth metal cations such as magnesium or calcium, or ammonium cation including e.g. the cations derived from an organic nitrogen-containing base, such as trialkylamine-derived cations for example triethylammonium ion.

The term "alkyl" is meant to encompass a monovalent linear (unbranched), branched or cyclic saturated hydrocarbon radical. When referring to "$C_1$-$C_6$ alkyl" it should be understood to encompass any linear or branched alkyl having 1, 2, 3, 4, 5, or 6 carbon atoms. Non-limiting examples of $C_1$-$C_6$ alkyl include methyl, ethyl, n-propyl, iso-propyl, n-butyl, 2-butyl, 3-butyl, n-isobutyl, 2-isobutyl, n-pentyl, 2-pentyl, 3-pentyl, 2-methylbutyl, 2-dimethylpropyl, n-hexyl, 2-hexyl, 3-hexyl, 2-methylpentyl, 3-methylpentyl, 2,3-dimethylbutyl, 2,2-dimethylbutyl, 2-methyl-2-ethyl-propyl, cyclobutyl, 1-methyl-clyclobutyl, 2-methyl-cyclobutyl, 1,1-dimethyl-cyclobutyl, 1,2-dimethyl-cyclobutyl, 2,2-dimethyl-cyclobutyl, methyl-1-cyclobutyl, 1-cyclobutyl-ethyl, 2-cyclobutyl-ethyl, cyclopentyl, 1-methyl-cyclopentyl, 2-methyl-cyclopentyl. Similarly, when referring to "—$C_{10}$-$C_{30}$ alkyl" it should be understood to encompass any linear or branched alkyl radical having 10, 11, 12, 13, 14, 15, 16, 17, 18, 19, 20, 21, 22, 23, 24, 25, 26, 27, 28, 29 30 carbon atoms. Similarly, when referring to "—$C_{11}$-$C_{20}$ alkyl" it should be understood to encompass any linear or branched alkyl radical having 11, 12, 13, 14, 15, 16, 17, 18, 19, 20 carbon atoms. Similarly, when referring to "—$C_{13}$-$C_{22}$ alkyl" it should be understood to encompass any linear or branched alkyl radical having 13, 14, 15, 16, 17, 18, 19, 20, 21, 22 carbon atoms.

The term "alkenyl" is meant to encompass a linear (unbranched) or branched hydrocarbon chain having at least one double bond. A double bond may be between any two carbon atoms of the alkenyl chain and may be in the cis or trans (or the E or Z) configuration. A double bond of an alkenyl may be unconjugated or conjugated to another unsaturated group. When referring to "—$C_{13}$-$C_{22}$ alkenyl" it should be understood to encompass any linear or branched alkenyl radical having 13, 14, 15, 16, 17, 18, 19, 20, 21, 22 carbon atoms. Similarly, when referring to "—$C_{11}$-$C_{20}$ alkenyl" it should be understood to encompass any linear or branched alkenyl radical having 11, 12, 13, 14, 15, 16, 17, 18, 19, 20 carbon atoms. Similarly, when referring to "—$C_{10}$-$C_{30}$ alkeyl" it should be understood to encompass any linear or branched alkyl radical having 10, 11, 12, 13, 14, 15, 16, 17, 18, 19, 20, 21, 22, 23, 24, 25, 26, 27, 28, 29 30 carbon atoms The term "alkynyl" is meant to encompass a linear (unbranched) or branched hydrocarbon chain having at least one triple bond. The triple bond may be between any two carbon atoms of the alkynyl chain. The triple bond of an alkynyl may be unconjugated or conjugated to another unsaturated group. When referring to "—$C_{13}$-$C_{22}$ alkynyl" it should be understood to encompass any linear or branched alkynyl radical having 13, 14, 15, 16, 17, 18, 19, 20, 21, 22 carbon atoms. Similarly, when referring to "—$C_{11}$-$C_{20}$ alkynyl" it should be understood to encompass any linear or branched alkynyl radical having 11, 12, 13, 14, 15, 16, 17, 18, 19, 20 carbon atoms. Similarly, when referring to "—$C_{10}$-$C_{30}$ alkynyl" it should be understood to encompass any linear or branched alkyl radical having 10, 11, 12, 13, 14, 15, 16, 17, 18, 19, 20, 21, 22, 23, 24, 25, 26, 27, 28, 29 30 carbon atoms.

The term "phenyl" should be understood to mean the aromatic cyclic group having the formula $C_6H_5$. The term "phenol" should be understood to mean the aromatic group having the formula $C_6H_4OH$, wherein said —OH group may be substituted at any point on the cyclic ring.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent, the substituents may be the same or different.

In another aspect, the invention encompasses a pharmaceutical composition comprising a fatty acid amide as disclosed herein including any stereoisomer and salt thereof. The invention further provides a pharmaceutical composition comprising at least one fatty acid amide as disclosed herein including any stereoisomer and salt thereof, in combination with at least one other therapeutic agent. The invention further provides a use of a fatty acid amide disclosed herein for the preparation of a pharmaceutical composition.

The present invention also relates to a pharmaceutical composition comprising a fatty acid amide disclosed herein in combination (e.g., admixture) with a pharmaceutically acceptable auxiliary, and optionally at least one additional therapeutic agent. The auxiliary must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant.

In some embodiments a pharmaceutical composition disclosed herein is a transdermal composition. In some other embodiments said fatty acid amide disclosed herein is administered to a patient using a transdermal formulation. In some embodiments, said transdermal formulation/composition employs the use of a dermal patch.

In some embodiments a pharmaceutical composition disclosed herein is a nasal composition. In some other embodiments said fatty acid amide disclosed herein is administered to a patient using a nasal formulation. In some embodiments, said nasal formulation/composition employs the use of a delivery device (for example a nebulizer).

The compositions may be prepared by any method well known in the art of pharmacy. Such methods include the step of bringing in association fatty acid amides of the invention or combinations thereof with any auxiliary agent. The auxiliary agent(s), as the accessory ingredient(s), is typically selected from those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions may further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the effect to be achieved and may vary with the particular formula, the route of administration, and the age and condition of the individual subject to whom the composition is to be administered.

The invention further provides a kit comprising at least one compound of the invention or a pharmaceutical composition comprising thereof, as hereinbefore described, and instructions for use thereof.

The present invention also provides a method of treatment of a patient suffering from an addiction disorder including any condition and symptom associated therewith; comprising administering to said patient at least one fatty acid amide of an amino acid, including a stereoisomer and a salt thereof.

The present invention provides a method of treatment of substance abuse disorder, including conditions and symptoms associated therewith, said method comprises administering to a patient at least one fatty acid amide of an amino acid, including a stereoisomer and a salt thereof.

In a further aspect the invention provides a method of treatment of a patient suffering from an addiction to a substance including any disorder, condition and symptom associated therewith; said method comprises administering to a patient at least one fatty acid amide of an amino acid, including a stereoisomer and a salt thereof.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 3A-3C shows the representative chromatograms describing the presence of OlGly in the insula of TBI mice but not sham or naïve mice. (3A(1)) Injured insula shows formation of OlGly as confirmed by MS and MS/MS spectra. In sham mice (3B), as well as in naïve mice (3C), endogenous OlGly is not detectable at the retention time of synthetic OlGly shown by the arrow. FIG. 3A(2) chromatogram traces represent the total ion current (TIC), and FIG. 3A(3) chromatogram traces represent the extracted chromatograms m/z around 340 amu.

FIGS. 7A-7L show the increased endogenous cannabinoids in the reward system in cocaine sensitized mice following sensitization. Mice were sacrificed and Nucleus Accumbens (FIGS. 7A-7F) and hippocampus (FIG. 7G-7L) were dissected and analyzed for the different compounds. Results are presented for OlGl (oleoyl glycine) (FIGS. 7A and 7G), 2-AG (2-arachidonoyl glycerol, an endogenous cannabinoid) (FIGS. 7B and 7H), OS (oleoyl serine) (FIGS. 7C and 7I), AEA (arachidonoyl ethanolamide, anandamide, an endogenous cannabinoid) (FIGS. 7D and 7J), PEA (palmitoyl ethanolamide) (FIGS. 7E and 7K), OEA (oleoyl ethanolamide) (FIGS. 7F and 7L). *p<0.001 saline vs cocaine It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

Figure 1:
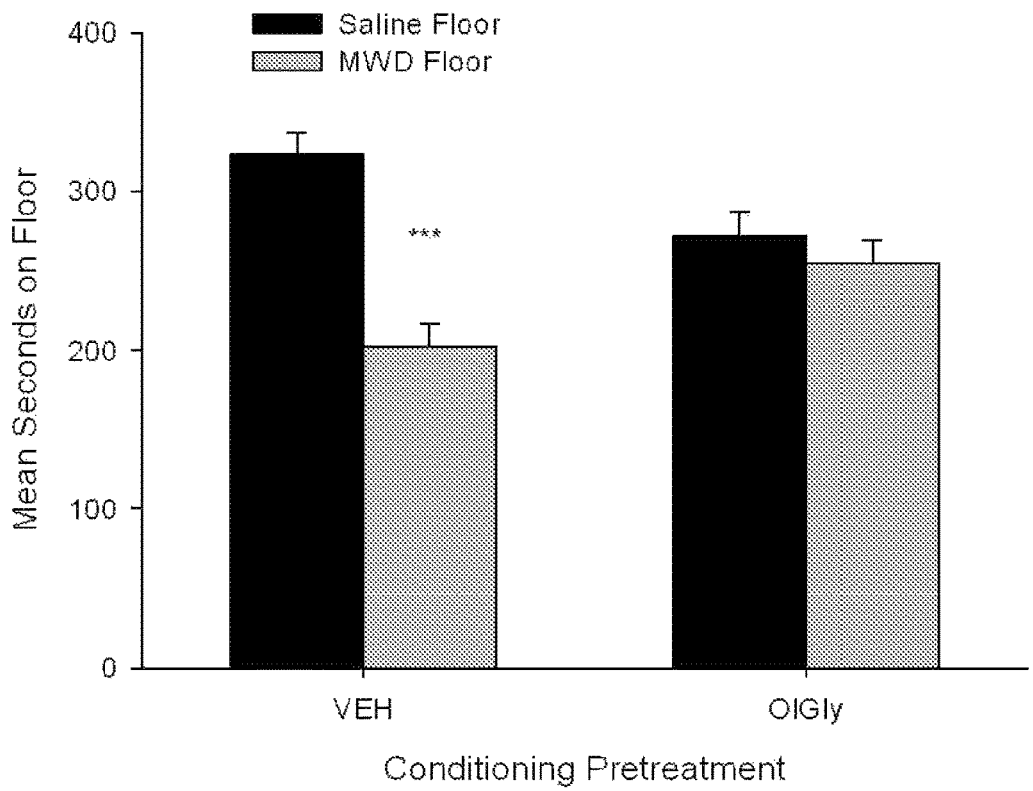
FIG. 1 shows the mean (±sem) time spent in seconds on the saline-paired floor and the MWD-paired floor during the drug free test trial by rats treated with VEH or 5 mg/kg OlGly during each MWD trial in Experiment 2. Asterisks indicate a significant difference between the saline and morphine withdrawal paired floors, ***p<0.001.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Part I: Oleoyl Glycine Interferes with Morphine Withdrawal, but not Morphine Reward Subjects Male Sprague-Dawley rats (200 g to 250 g) were used as subjects. Animals were pair-housed in an opaque shoebox cage while receiving food and water ad libitum. They were exposed to a 12/12 h reverse light/dark cycle where the lights turn on at 7 p.m. All experiments were conducted during the rats' dark cycle. The colony room housing all of the rats was kept at 21° C. All animal procedures were approved by the Animal Care Committee of the University of Guelph and adhere to the guidelines of the Canadian Council of Animal Care.

Drugs

Morphine and naloxone were prepared with saline at a concentration of 20 and 1 mg/ml, respectively, before injecting subcutaneously (sc) at a volume of 1 ml/kg. OlGly and AM251 were dissolved in a vehicle mixture of ethanol, Tween 80, and physiological saline in a 1:1:18 ratio. Oleoyl glycine and AM251 were both first dissolved in ethanol, Tween 80 was then added to the solution, and the ethanol was evaporated off with a nitrogen stream; after which, the saline was added. The final vehicle (VEH) consisted of 1:9 (Tween/saline). Oleoyl glycine was prepared at a concentration of 5 mg/ml or 30 mg/ml and injected i.p.

Apparatus

A place conditioning apparatus with removable floors was used. The conditioning apparatus was a rectangular box (60×25×25 cm) made of black Plexiglas and a wire mesh lid. During conditioning, removable metal floors characterized by either a holed surface (1 cm in diameter spaced 1 cm apart from each other) or a grid surface (½ cm horizontal bars spaced 1 cm apart) were placed upon a black rubber mat on top of the black Plexiglas surface. The different floors act as contextual cues that differentiate the treatment floor and the VEH floor. During the test and pre-test trials, black metal floors split into two equal halves (half holed and half grid surface) were placed into the conditioning boxes. The tactile stimulus properties of the two floor halves were identical to their matching floor counterparts used in conditioning. Ethovision software was employed to define box and floor type perimeters, as well as to define a neutral zone.

Procedure

All rats received a 10 min drug-free pretest trial to measure baseline floor preferences. Ethovision tracked the movement of rats throughout the trial to determine how much time was spent on each floor. Each rat was then assigned to a specific drug group and drug floor (hole or grid floor) in a counterbalanced manner. Rats with a bias of more than 200 s for either floor were removed. Floors and conditioning boxes were washed between each trial.

Experiment 1: Potential of OlGly to Produce a CPP or CPA

Rats (n=12) received two conditioning trials with oleoyl glycine. On each trial they received intraperitoneal (ip) injections of 5 mg/kg oleoyl glycine or VEH (24 hr apart; counterbalanced order) 20 minutes prior to placement in the conditioning box lined with the grid or hole floor (counter-balanced) for 20 minutes. Three days after the final conditioning day, the rats received a 10 min drug-free test trial with the split grid/hole floor.

Experiment 2: Effect of Systemic OlGly on the Establishment of a Naloxone Precipitated MWD-CPA Rats (n=22) received two 3-day conditioning cycles in order to attain a naloxone precipitated MWD-induced place avoidance. On Day 1, the floor opposite to the assigned drug floor was paired with a s.c. saline injection. Ten minutes after a saline injection, the rats were placed into the conditioning box with the assigned saline-paired floor for 20 minutes while their locomotion was tracked with Ethovision. On Day 2, the rats received a high dose of morphine (20 mg/kg) s.c., 24 h after the saline conditioning trial the previous day. After the injection, they were placed in an empty shoebox cage and monitored for signs of respiratory distress and stimulated when necessary until they recovered and were returned to the home cage. On Day 3, 24 h post morphine injections, the rats were injected with either VEH (n=12) or OlGly (n=12) 10 min prior to receiving an s.c. injection of naloxone. Ten min later they were placed into the conditioning box with the assigned naloxone-paired floor for 20 minutes while their locomotion was tracked using Ethovision. Four days later, all rats underwent a second 3-day conditioning cycle. Five days following the last naloxone trial, a 10 min drug-free test trial was performed. The test trial consisted of the same procedures as the pre-test trial, but rats were given a s.c. saline injection 10 min prior to the test. During the test trial, Ethovision tracked the amount of time the rats spent on each floor surface.

Experiment 3: Effect of Systemic OlGly on the Establishment of a Morphine Induced CPP Rats received four 2-day conditioning trials in order to produce a morphine-induced conditioned place preference. During each conditioning trial, all rats received an s.c. injection of morphine (10 mg/kg) on one day and saline on the other day (in a counterbalanced order), ten min prior to being placed into the conditioning chamber with a morphine or saline paired floor, respectively, for a duration of 30 min. On the morphine conditioning trial, the rats were administered an i.p. injection of VEH (n=11), 5 mg/kg OlGly (n=11) or 30 mg/kg OlGly (n=10) 10 min prior to the morphine injection. On the saline conditioning trial, all rats were injected with VEH 10 min prior to the saline injection. Three days after the final conditioning day, the rats received a 10 min drug-free test trial with the split grid/hole floor. All rats received an s.c. administration of saline 10 minutes prior to each test trial.

Results

Experiment 1: Potential of Oleoyl Glycine to Produce a CPP or CPA

OlGly did not produce a significant preference or aversion for the drug paired floor, t (11)=0.09, ns. Rats spent an equal amount of time on the VEH paired floor (M=232.16 sec, ±36.44) as they did on the oleoyl glycine paired floor (M=299.00 sec, ±36.44). Furthermore, an activity measure revealed no motoric effects of oleoyl glycine compared to VEH during conditioning.

Experiment 2: Effect of Systemic Oleoyl Glycine on the Establishment of MWD-CPA

OlGly significantly interfered with the establishment of the naloxone precipitated MWD-induced CPA. FIG. 1 shows the mean (±sem) number of sec spent on the saline-paired floor and the MWD-paired floor on the drug free test trial by rats that received VEH or oleoyl glycine during each MWD trial in Experiment 2. The 2×2 mixed factors ANOVA with between group factor of pretreatment drug (VEH, 5 mg/kg OlGly) and the within group factor of floor (MWD, saline) revealed a significant drug by floor interaction, F (1, 20)=6.80, p=0.017. Subsequent paired t-tests revealed that there was a floor aversion only in group VEH t (11)=4.59, p<0.001. Evaluation of activity during the conditioning trials revealed a significant effect of conditioning drug, F (1, 20)=118.75; p<0.001, whereby rats were significantly less active during naloxone conditioning trials than saline conditioning trials, but pretreatment with OlGly did not modify activity.

Figure 2:
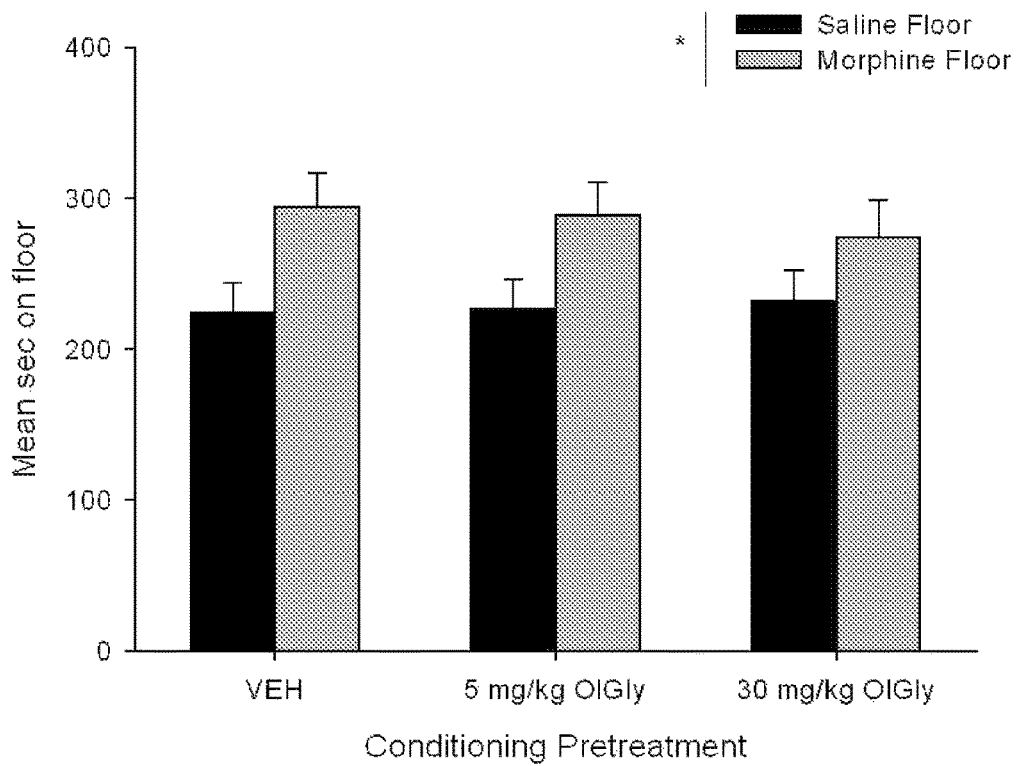
FIG. 2 shows the mean (±sem) time spent in seconds on the saline-paired floor and the morphine-paired floor during the drug free test trial by rats that received VEH, 5 mg/kg oleoyl glycine or 30 mg oleoyl glycine during the morphine conditioning trial in Experiment 4. Asterisks indicate a significant overall preference for the morphine paired floor across groups *p=0.025

Experiment 3: Effect of Systemic OlGly on the Establishment of a Morphine-Induced CPP At 5 or 30 mg/kg, OlGly did not modify the establishment of a morphine-induced place preference. FIG. 2 presents the mean (±sem) number of sec spent on the saline-paired and the MWD-paired floor during the drug free test trial by rats that received VEH, 5 mg/kg or 30 mg/kg OlGly during each MWD conditioning trial. A 3×2 mixed factors ANOVA with between group factor of pretreatment drug (VEH, 5 mg/kg OlGly, 30 mg/kg OlGly) and the within group factor of floor (morphine, saline) revealed only a significant effect of floor, F (1, 31)=5.62, p=0.025, with no significant drug by floor interaction. Overall, all rats displayed a morphine-induced CPP, but systemic OlGly administrations did not alter that preference. Furthermore, evaluation of activity during the conditioning trials revealed a significant effect of trial, F (1, 31)=26.40; p<0.001, whereby rats were significantly less active during morphine conditioning trials than saline conditioning trials, but pretreatment with OlGly did not modify activity.

Part II: Oleoyl Glycine Produced by Brain Trauma Reduces Nicotine Reward and Withdrawal in Mice Animals Male C57BL/6 mice (Charles River, Italy) weighing 18-20 g were used for the mild TBI Weight Drop (WD) model. Mice were housed three per cage under controlled illumination (12 h light/dark cycle; light on 6:00 A.M.) and standard environmental conditions (ambient temperature 20-22° C., humidity 55-60%) for at least 1 week before the beginning of experiments. Animal chow and tap water were available ad libitum. Male ICR mice (6-8 weeks old; Harlan, Indianapolis, Ind.) with a body mass of 27-32 g served as subjects in all in vivo pharmacology experiments. Mice were group-housed (four per cage) on a 12/12 light/dark cycle (lights on at 0600 h) and given food and water ad libitum. All animal protocols were approved by the Virginia Commonwealth University Institutional Animal Care and Use Committee, were in accordance with the National Institutes of Health Guide for the Care and Use of Laboratory Animals (Institute of Laboratory Animal Resources, 2011), and by the Animal Ethics Committee of The Second University of Naples, in compliance with Italian (D.L. 116/92) and European Commission (O.J. of E.C. L358/1 18/12/86) regulations on the protection of laboratory animals. All efforts were made to reduce both animal numbers and suffering during the experiments.

Surgical Preparation and Injury (Mouse WD Model)

Experimental mild TBI (mTBI) was performed using a weight-drop device developed in the Naples laboratory. Mice were anesthetized with intraperitoneal injection of 250 mg/kg Avertin before being subjected to mTBI. After a midline longitudinal incision, the skull was exposed to locate the area of impact and placed under a metal tube device where the opening was positioned directly over the animal's head. The injury was induced by dropping a cylindrical metal weight (50 g), through a vertical metal guide tube from a height of 20 cm. The point of impact was between the anterior coronal suture (bregma) and posterior coronal suture (lambda). Immediately following injury the skin was closed with surgical wound clips and mice were placed back in their cages to allow for recovery from the anesthesia and mTBI. Sham mice were submitted to the same procedure as described for mTBI, but without release of the weight.

Drugs $[^2H]_8$AEA, $[^2H]_5$2-AG, $[^2H]_4$ PEA, $[^2H]_4$ OEA, $[^2H]_8$ N-arachidonoyldopamine (NADA), $[^2H]_8$AraSer and $[^2H]_8$AraGly were purchased from Cayman Chemicals (MI, USA). OlGly was synthetized in the Mechoulam laboratory and CP55,940 ((−)-cis-3-[2-hydroxy-4-(1,1-dimethylheptyl) phenyl]-trans-4-(3-hydroxypropyl)cyclohexanol) and morphine sulfate were generously provided by NIDA (Rockville, Md.). OlGly and CP55,940 were dissolved in a vehicle solution consisting of ethanol (5% of total volume), alkamuls-620 (Sanofi-Aventis, Bridgewater, N.J.) (5% of total volume), and saline (0.9% NaCl) (90% of total volume). Oleoyl glycine and CP55,940 were given via the intraperitoneal (i.p.) route of administration. (−)-Nicotine hydrogen tartrate [(−)-1-methyl-2-(3-pyridyl)pyrrolidine (+)-bitartrate] and mecamylamine HCl were purchased from Sigma-Aldrich Inc. (St. Louis, Mo., USA). Morphine sulfate [morphine hemi[sulfate pentahydrate]] Nicotine and mecamylamine (2 mg/kg) were dissolved in physiological saline and given via the subcutaneous (s.c.) route of administration in a volume of 10 ml/kg. For the nicotine CPP study, 0.5 mg/kg nicotine dose was used because this dose reliably produces significant CPP in ICR mouse (18). Morphine CPP was performed with 10 mg/kg (s.c.) as recently described (19). For nicotine withdrawal studies, 24 mg/kg/day nicotine or saline was continuously perfused for 14 days using s.c. osmotic minipumps (model 2000; Alzet Corporation, Cupertino, Calif.) that were implanted under isoflurane anesthesia. This prolonged nicotine administration regimen reliably produces significant withdrawal syndrome in the three behavioral paradigms used here.

Synthesis of Oleoyl Glycine

To a solution of oleic acid (1 gm, 3.54 mmol) and N,N-dimethylformamide (266 µL, 3.64 mmol) in dry methylene chloride (10 mL) was added dropwise oxalyl chloride (2.0 M solution in methylene chloride, 3.5 mL, 7 mmol) under nitrogen atmosphere. The reaction mixture was stirred for 1 h and then the solvent was evaporated under a nitrogen flow. The crude material in methylene chloride (10 mL) was added to a solution of glycine (800 mg, 10.62 mmol) and 2 N potassium hydroxide in an ice bath. Then, the reaction mixture was stirred for 1 h, water (10 mL) was added, and the mixture was acidified to pH 3 with 1 N HCl. The product was extracted with ether (3×50 mL) and dried (MgSO$_4$), and solvent was evaporated under reduced pressure. The crude material was chromatographed on silica gel (eluting with chloroform:methanol) to yield a crystalline solid. Melting point 93-94 C (degradation); LC-MS: (M−H)$^+$=339 m/z; NMR (CD$_3$OH, ppm): 5.35-5.32 (m, 2H), 4.45 (s, 2H), 2.13-2.18 (m, 6H), 1.58 (m, 2H), 1.32-1.29 (m, 20H), 0.88 (t, 3H).

Extraction and Quantification of endocannabinoids, N-acylethanolamines, N-acyldopamines, N-acylserines and N-acylglycines Brain tissues were frozen in liquid nitrogen immediately after dissection, which took place within 5 min from sacrifice. Frozen tissues were then dounce-homogenized and extracted with chloroform/methanol/Tris-HCl 50 mM pH 7.5 (2:1:1, v/v) containing internal deuterated standards for AEA, 2-AG, PEA, OEA, NADA, AraSer and AraGly quantification by isotope dilution (10 pmol for $[^2H]_8$AEA; 50 pmol for $[^2H]_5$2-AG, $[^2H]_4$ PEA and $[^2H]_4$ OEA; 5 pmol for $[^2H]_8$ NADA, $[^2H]_8$AraSer and $[^2H]_8$AraGly). Then the lipid extract was purified by open bed chromatography on silica. Fractions were eluted within increasing amounts of CH$_3$OH in CHCl$_3$ and part of the 9:1 (v/v) fraction was analyzed by liquid chromatography-atmospheric pressure chemical ionization-single quadrupole mass spectrometry for AEA, 2-AG, PEA and OEA levels, as previously described (22, 23). AEA, 2-AG, PEA and OEA levels were calculated on the basis of their area ratio with the internal deuterated standard signal areas. Part of the 9:1 fraction was used for N-acyldopamine identification, whereas the 7:3 fraction was used for N-acylglycine and N-acylserine identification and quantification by LC-MS-IT-TOF (Shimadzu Corporation, Kyoto, Japan) equipped with an ESI interface, using multiple reaction monitoring (MRM). The method for NADA was as previously described. Quantification was performed by isotope dilution by using m/z values of 370.3192 and 362.2692 corresponding to the molecular ion [M+H]$^+$ for deuterated and undeuterated AraGly; or m/z values of 400.3297 and 392.2795 corresponding to the molecular ion [M+H]$^+$ for deuterated and undeuterated AraGly. The recovery of AraGly and AraSer from rat brain tissues using the extraction and analytical procedure reported here (see Methods) was 49.1±15.7% and 42.1±15.9% (n=7). The LC-ESI-IT-ToF method was specific and exhibited a limit of detection (LOD, defined as the concentration at which the signal/noise ratio is greater than 3:1) of 50 fmol in the MS mode, and 1 pmol in the MS/MS mode for all the compounds analysed. Moreover, the ratio between the [M+H]$^+$ peak areas of undeuterated (0.025-10 pmol) vs. deuterated (1 pmol) AraGly and AraSer varied linearly with the amount of the respective deuterated standards. The quantification limit of compounds was 100 fmol and the reproducibility of the method was 95%-99%. The chromatograms of the high-resolution [M+H]$^+$ values were extracted and used for calibration and quantification. LC analysis was performed in the isocratic mode using a Kinetex C18 Column (10 cm×2.1 mm, 5 μm) and CH$_3$OH/water/acetic acid (85:15:0.1 by vol.) as the mobile phase with a flow rate of 0.15 ml/min. Identification of N-acyldopamines, N-acylglycines and N-acylserines was carried out using ESI ionization in the positive mode with nebulizing gas flow of 1.5 ml/min and curved desolvation line temperature of 250° C.

Conditioned Place Preference (CPP) Studies

An unbiased CPP paradigm was performed, as previously described. Briefly, the CPP apparatus consisted of three chambers in a linear arrangement (MedAssociates, St. Albans, Vt., ENV3013) with white and black chambers (20×20×20 cm each), which also differed in floor texture (white mesh or black rod). These chambers were separated by a small gray chamber with a smooth PVC floor. Partitions could be removed to allow access from the gray chamber to the black and white chambers. On day 1, animals were confined to the middle chamber for a 5-min habituation period and then allowed to move freely among all three chambers for 15 min. Time spent in each chamber was recorded, and no systematic bias was observed in baseline chamber preference. Twenty-min conditioning sessions occurred twice a day (days 2-4). During conditioning sessions, mice were confined to one of the larger chambers. The control group received saline in one large chamber in the morning and saline in the other large chamber in the afternoon. The nicotine group received nicotine in one large chamber and saline in the other large chamber. Treatments were counterbalanced equally in order to ensure that some mice received nicotine in the morning while others received it in the afternoon. The nicotine-paired chamber was randomized among subjects. Sessions were 4 h apart and were conducted by the same investigator. On each of the conditioning days, mice were pretreated with OlGly (i.p.) or vehicle 15 min prior to nicotine or morphine (s.c.) injection. Five min after nicotine administration, subjects were given 20-min conditioning sessions. In the morphine CPP comparison study, mice were given 30 min conditioning sessions following a 15 min pretreatment of morphine (10 mg/kg, s.c.) (19). On test day (day 5), mice were allowed access to all chambers for 15 min in a drug free state. The preference score was calculated by determining the difference between the time spent in the drug paired side during test day versus the time in drug paired side during the baseline day.

Nicotine Precipitated Withdrawal Studies

Mice were implanted with subcutaneous osmotic minipumps (model 2000; Alzet Corporation, Cupertino, Calif.) under isoflurane anesthesia. The pumps delivered 24 mg/kg/day nicotine or saline for 14 days. The concentration of nicotine was adjusted according to animal weight and mini pump flow rate. On the morning of day 15, mice were given a s.c. injection of the non-selective nicotinic acetylcholine receptor (nAChR) antagonist mecamylamine (2 mg/kg, s.c.) and 15 min later administered vehicle or OlGly (10, 30, and 60 mg/kg, i.p.). Beginning 10 min following mecamylamine administration affective (anxiety-like behavior) and physical (somatic signs, hyperalgesia) nicotine withdrawal signs were assessed as previously described (24). Mice were first evaluated for 5 min in the plus maze test for anxiety-related behavior. The duration of time spent on the open arms of the plus maze was assessed as a measure of anxiety-related response. The number of arm crosses between the open and closed arms was also counted as a measure of locomotor activity. The plus maze assessment was immediately followed by a 20-min observation of somatic signs measured that included paw and body tremors, head shakes, backing, jumps, curls, and ptosis. Mice were placed in clear activity cages without bedding for the observation period. The total number of somatic signs was tallied for each mouse and the average number of somatic signs during the observation period was plotted for each test group. Hyperalgesia was evaluated using the hot plate test immediately following the somatic signs observation period. Mice were placed into a 10-cm wide glass cylinder on a hot plate (Thermojust Apparatus, Richmond, Va.) maintained at 52° C. The latency to reaction time (jumping or paw licking) was recorded. The specific testing sequence was chosen based on our prior studies showing that this order of testing reduced within-group variability and produced the most consistent results (24). All studies were performed by an observer blinded to experimental treatment.

Tetrad Behavioral Assessment

Mice were acclimated to the test environment for at least 1 h prior to testing for tetrad components: spontaneous activity, catalepsy, antinociception, and hypothermia (7-9). In the locomotor studies, subjects were administered vehicle or drug and 5 min later were placed into clear acrylic boxes (approx. 44.5 cm×22.25 cm×20.0 cm) contained within sound-attenuating cabinets equipped with an LED light source and fans for general air circulation and creation of white noise. The distance traveled (cm) and time spent immobile (s) for each mouse were collected and recorded for 10 min using Fire-i™ digital cameras purchased from Unibrain (San Ramon, Calif., USA) and ANY-maze™ video tracking software purchased from Stoelting Company (Wood Dale, Ill., USA). Mice were assessed for baseline tail withdrawal latencies and body temperature, given an intraperitoneal (i.p.) injection of vehicle or drug (OlGly), and 30 min later assessed in the following order: catalepsy, tail withdrawal test, and body temperature. Catalepsy was measured using the horizontal bar test in which both fore limbs of the mouse were placed on a horizontal bar (approximately 1.25 cm in diameter and 4.5 cm parallel to the bench top), with the duration of a fixed and motionless posture (except normal breathing) recorded by stopwatch over a 60 s interval. Antinociception was determined in the warm water (52° C.) tail immersion test whereby the distal end (approximately 1 cm) of the tail was immersed into the water bath and the latency of the mouse to withdrawal its tail recorded (to the nearest 0.1 s). A 10 s cutoff was used to minimize tail damage. Antinociception data were transformed to represent a maximum percent effect (% MPE) by the following formula: % MPE=[(test latency−pretreatment latency)/(10−pretreatment latency)]×100. Body temperature measurements (recorded to the nearest 0.1° C.) were collected by inserting a rectal probe, lubricated with mineral oil and attached to a telethermometer (Yellow Spring Industries Inc., Yellow Springs, Ohio, USA), to a 2 cm depth.

Cumulative CP55,940 Dose-Response Study

Mice were pretreated with either OlGly (60 mg/kg i.p.) or vehicle 10 min before they received the first dose of CP55, 940 followed by each subsequent dose every 40 min. Measurements for catalepsy, tail-flick, and rectal temperature were taken 30 min following each CP55,940 administration, as well as prior to any injections to determine baseline responses. Cumulative doses of CP55,940 were 0.3, 1, and 3 mg/kg i.p. Locomotor activity was not assessed due to habituation effects that occur following repeated testing.

Statistical Analysis

Lipid levels are expressed as means±standard error (M±SEM) of pmols/g wet tissue weight, unless otherwise stated. One-way ANOVA followed by the Tukey's test was used for comparisons of AEA, 2-AG, PEA, OEA and OlGly levels among the various groups. P values lower than 0.05 were considered significant. For conditioned place studies, a preference score was calculated by subtracting time spent in the nicotine-paired chamber post-conditioning minus time spent pre-conditioning. A positive value indicated a preference for the nicotine- (or morphine-) paired compartment, whereas a negative value indicated an avoidance of the nicotine- (or morphine-) paired compartment. A number at or near zero indicated no preference. Data were analyzed by one-way ANOVA and further analyzed by the Student Neuman-Keuls post-hoc test. In tetrad studies and luciferase assay, data were analyzed by one-way ANOVA followed by the Dunnett's post-hoc test. In the cumulative dose-response of CP55,940, data were analyzed by two-way ANOVA followed by Sidak's post-hoc test. In the luciferase assay, the Student's t-test with Welch's correction was applied. A P value of <0.05 was considered statistically significant. In the binding studies, $K_i$ values were calculated by applying the Cheng-Prusoff equation to the IC50 values for the displacement of the bound radioligand by increasing concentrations of the test compound. The computer program GraphPad Prism version 6.0 (GraphPad Software Inc., San Diego, Calif.) was used in all statistical analyses. All data are expressed as mean+/−SEM.

Results

Figure 3B:
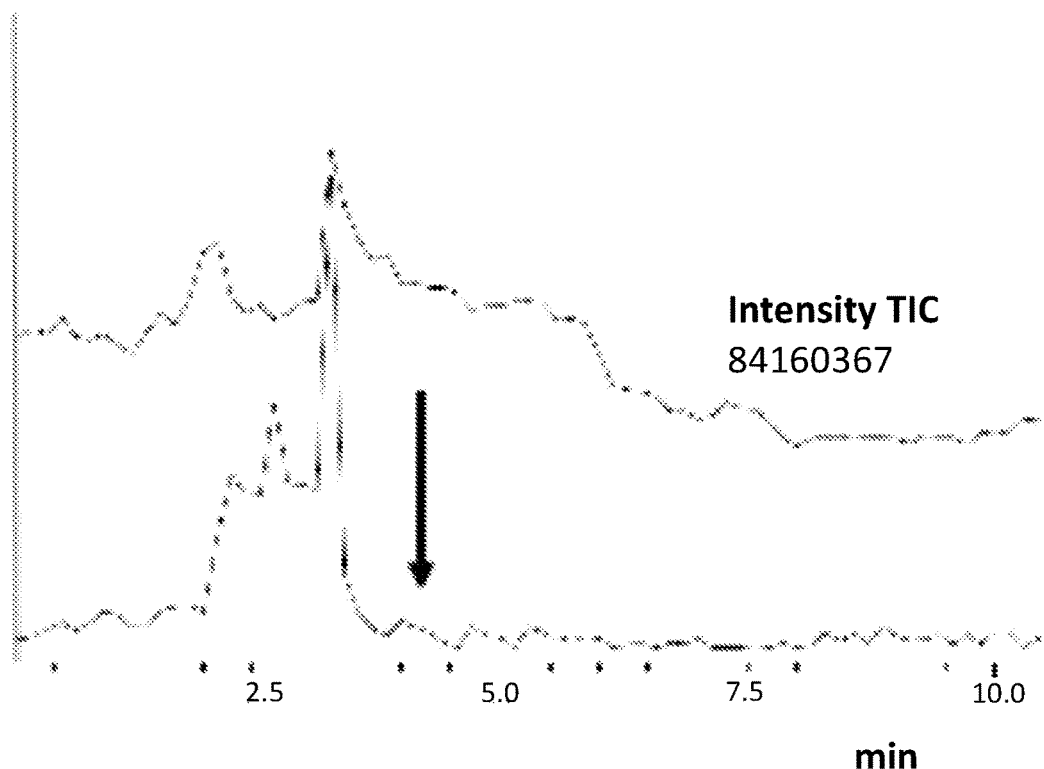
Figure 3C:
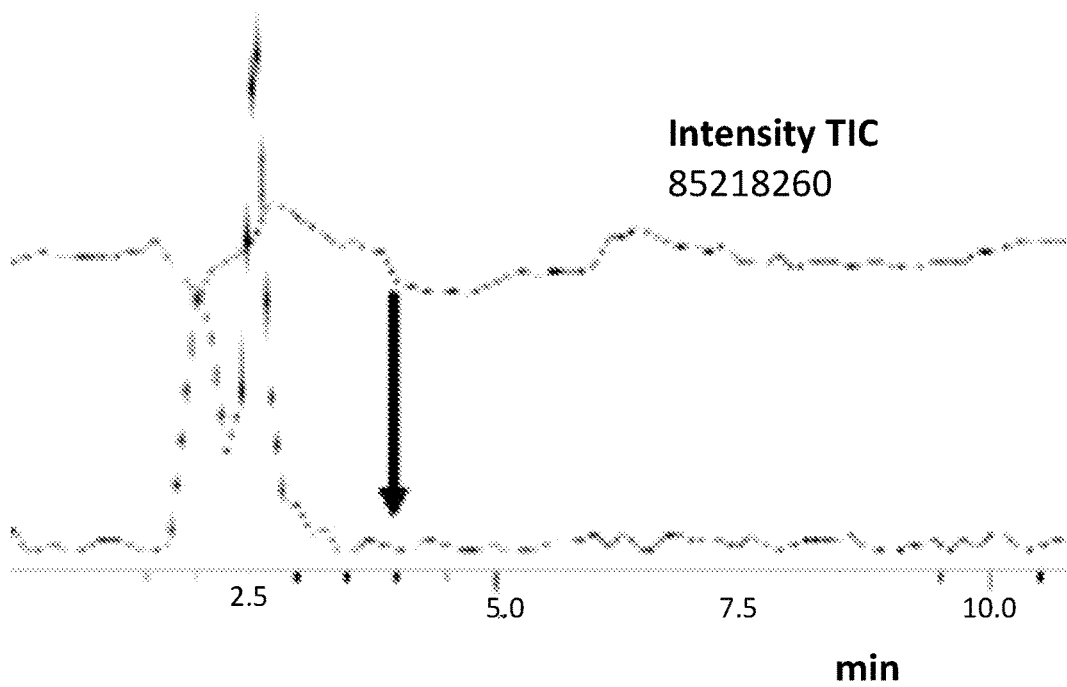

FIGS. 3A-3C shows the representative chromatograms describing the presence of OlGly in the insula of TBI mice but not sham or naïve mice. In FIG. 3A(1), the injured insula shows formation of OlGly as confirmed by MS and MS/MS spectra. In sham mice (FIG. 3B), as well as in naïve mice (FIG. 3C), endogenous OlGly is not detectable at the retention time of synthetic OlGly shown by the arrow. The chromatogram traces in FIG. 3A(2) represent the total ion current (TIC), and chromatogram traces in FIG. 3A(3) represent the extracted chromatograms m/z around 340 amu.

Figure 4:
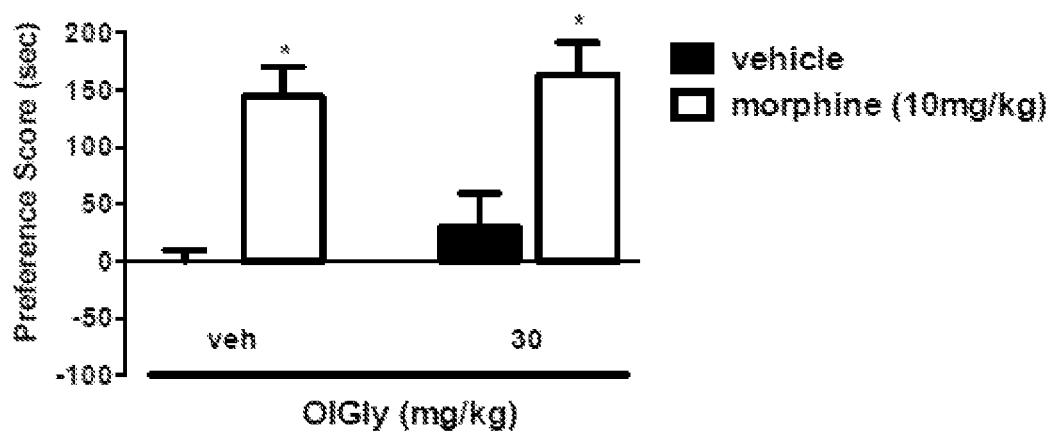
FIG. 4 shows OlGly has no effects on morphine-CPP. Mice were conditioned with either saline or morphine (10 mg/kg, s.c.) for 3 days. A robust CPP was observed in morphine-conditioned mice pre-treated with vehicle. OlGly did not attenuate expression of morphine CPP (30 mg/kg, i.p.). *p<0.05 vs. vehicle/vehicle. Values represent the mean±SEM of n=7-8 mice per group.
Figure 5A:
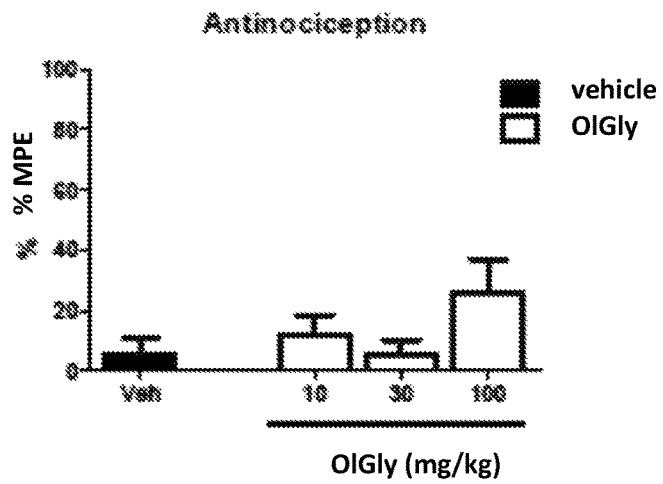
FIGS. 5A-5E shows the evaluation of cannabimimetic effects in the cannabinoid tetrad after OlGly administration. OlGly did not produce (5A) antinociception, (5B) hypothermia, or motor behavior, as reflected by the following measures: (5C) distance traveled, (5D) speed, and (5E) immobility time. Additionally, OlGly did not elicit cataleptic responses, as assessed in the bar test (data not shown). Values represent means±SEM of n=9 mice per group.
Figure 5B:
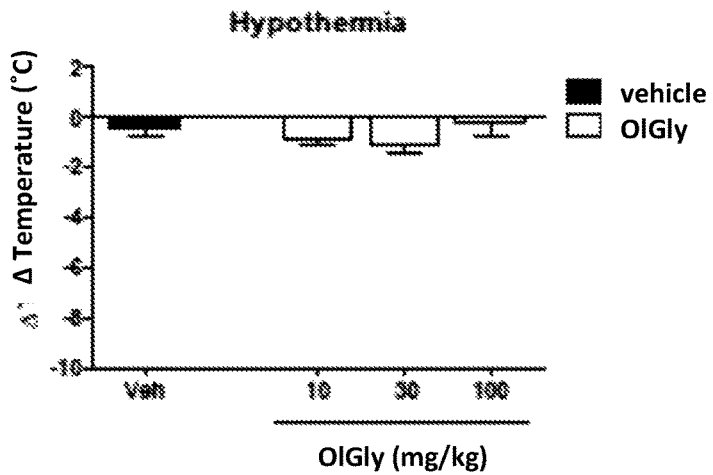
Figure 5C:
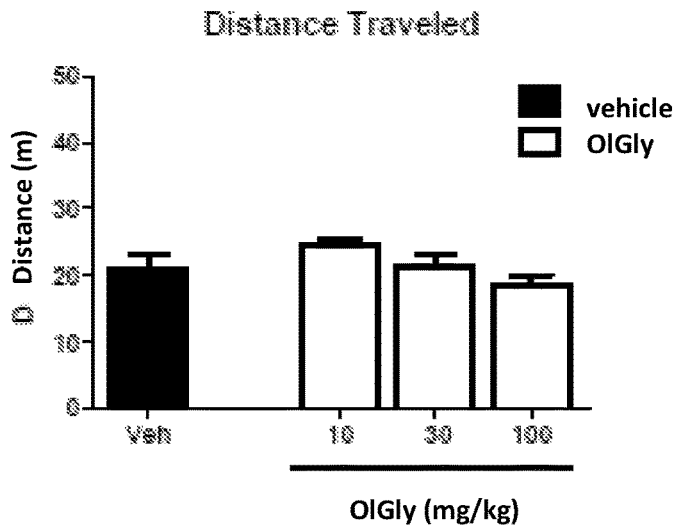
Figure 5D:
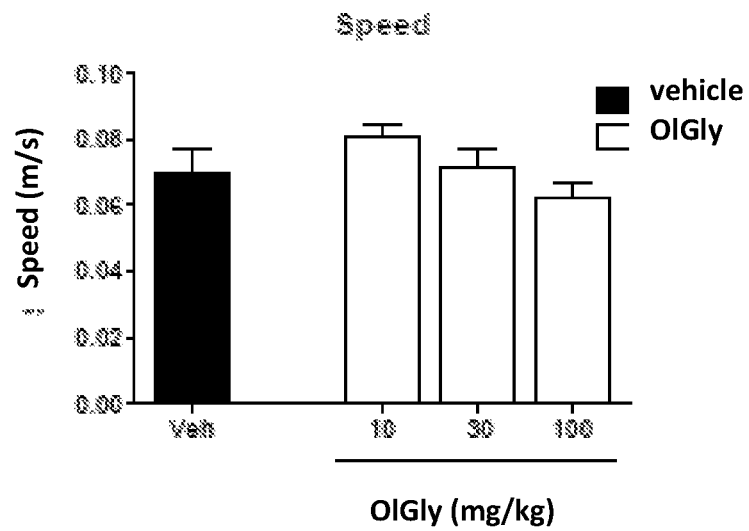
Figure 5E:
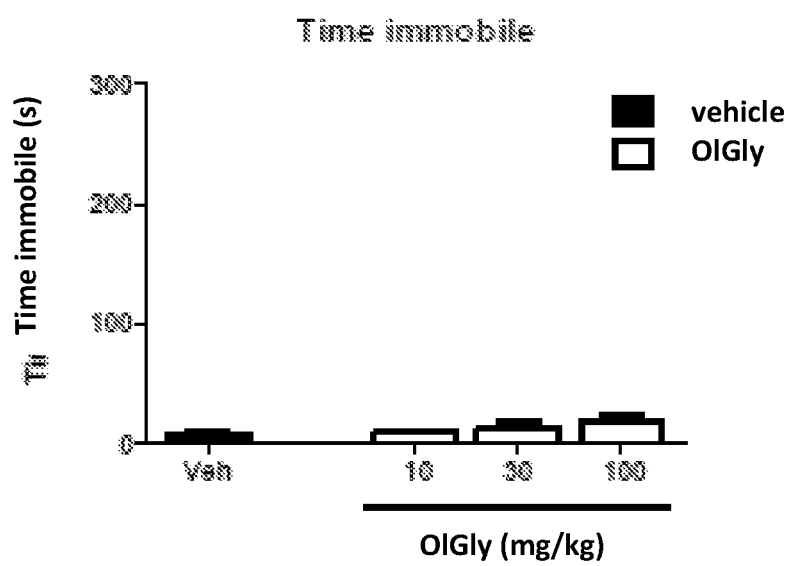

FIG. 4 shows that OlGly has no effects on morphine-CPP. Mice were conditioned with either saline or morphine (10 mg/kg, s.c.) for 3 days. A robust CPP was observed in morphine-conditioned mice pre-treated with vehicle. OlGly did not attenuate expression of morphine CPP (30 mg/kg, i.p.). *p<0.05 vs. vehicle/vehicle. Values represent the mean±SEM of n=7-8 mice per group.

FIGS. 5A-5E shows the evaluation of cannabimimetic effects in the cannabinoid tetrad after OlGly administration. OlGly did not produce (5A) antinociception, (5B) hypothermia, or motor behavior, as reflected by the following measures: (5C) distance traveled, (5D) speed, and (5E) immobility time. Additionally, OlGly did not elicit cataleptic responses, as assessed in the bar test. Values represent means±SEM of n=9 mice per group.

Part III: The Effect of OLGL-Like Molecules on the Acquisition of Cocaine-Induced Behaviors.

Figure 6:
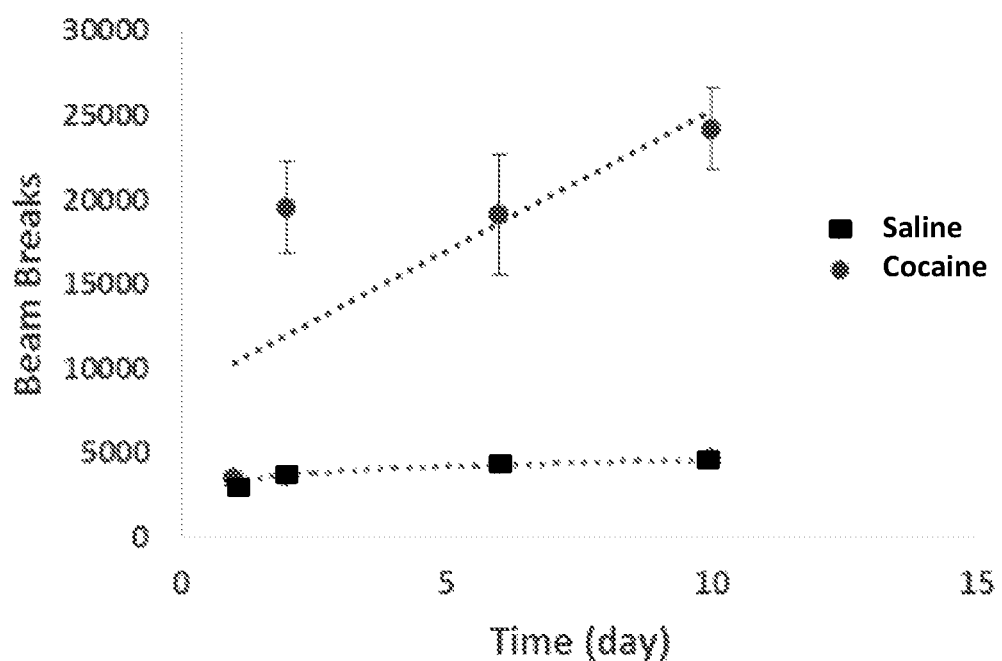
FIG. 6 shows the cocaine psychomotor sensitization following two days of habituation to the open field locomotor chamber, mice (n=10 in each group) were repeatedly injected with 20 mg/kg cocaine or saline for 10 days. Locomotor activity was monitored by number of beam breaks.
Figures 7G, 7H, 7I, 7J, 7K, 7L:
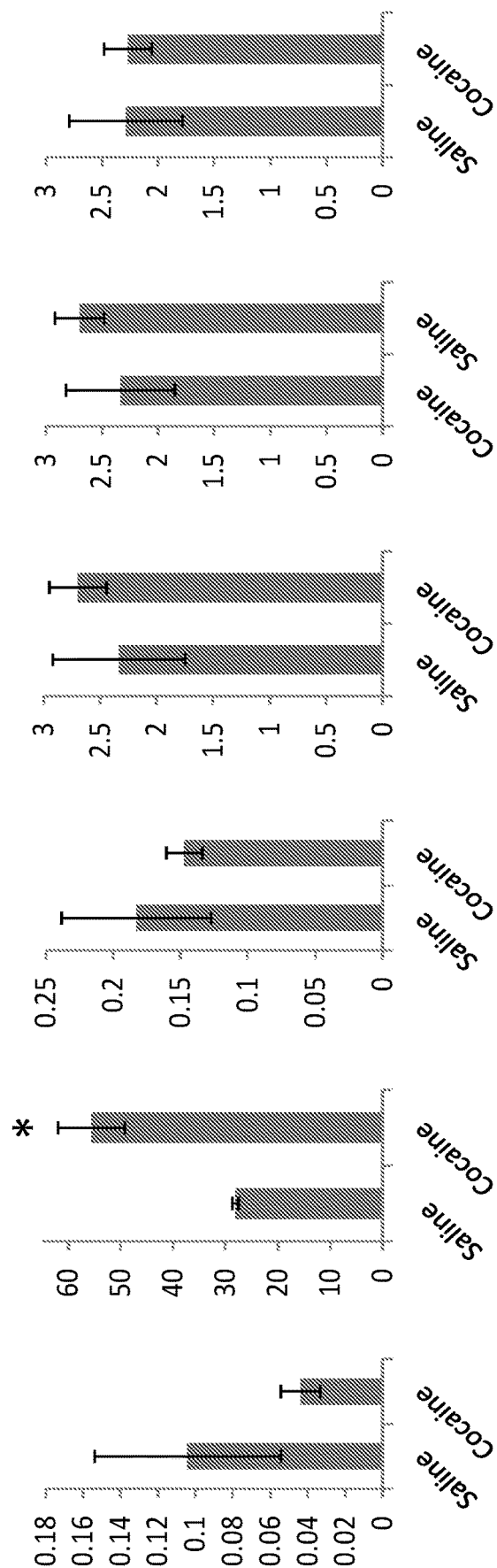

A preliminary sensitization protocol (Schumann et al., 2009) was conducted in order to examine whether endogenous defense system responds to drug insult. Therefore, mice received daily repeated injections of cocaine (20 mg/kg) for 10 days and their locomotion activity was measured. As shown in FIG. 6, animals developed sensitized response to chronic cocaine treatment (gradual increase in locomotion activity). On day 11, animals were sacrificed and the NAc and hippocampus were dissected and subjected to analysis for the levels of the various compounds. As clearly seen in FIGS. 7A-7L, the levels of OlGl were significantly increased in the NAC of cocaine treated mice. Likewise, the levels of 2AG, endogenous cannabinoid known to be neuroprotective (Panikashvily et al., 2001), increased in the hippocampus. Together these results suggested that this increase is related to a self-defense mechanism against cocaine insult.

We further show that boosting the endogenous system by exogenous administration of a compound of the invention such as oleoyl glycine, or compounds with similar characteristics, is beneficial for the prevention of the addictive state. Therefore, the effect of exogenous administration of OlGl and OlGl-like molecules in two different behavioral paradigms in addiction is tested: psychomotor sensitization (PS) and conditioned place preference (CPP). PS represents the increase in psychomotor response following repeated drug exposure which termed sensitized response and resemble the behavioral response of human addicts to drugs of abuse. CPP represents the preference of drug associated environment and resemble the reinforcing/rewarding properties of the drug in human addicts. First the ability of OLGL-like molecules are tested to affect the acquisition of BS and CPP. Sprague-Dawley rats (n=12 per group) is injected for the first two days with saline for habituation on the open field chambers, following habituation they are i.p. injected with 15 mg/kg of cocaine for 10 consecutive days (development phase of sensitization). Locomotor activity is continuously monitored during all behavioral sessions. The groups of animals for experiments are consisted of: cocaine injected group, OLGL (0.5; 5.0 and 10.0 mg/kg) or OLGL-like molecules prior to cocaine, saline injected groups and OLGL-like molecules prior to saline injection. The detailed procedure for PS is performed as described in Schumann and Yaka, 2009. Following the behavioral sessions animals are sacrificed and the levels of endogenous cannabinoids are determined.

To test the effect of OLGL-like molecules on reward are used CPP paradigm. Same groups as described above are conditioned for cocaine in the CPP apparatus as described in Beiser et al., 2017. Briefly, following habituation to the CPP chambers, same groups of rats (described above) are i.p. injected with cocaine 15 mg/kg or OLGL-like molecules prior to cocaine or saline injections every other day in different chambers. After 8 days of conditioning, rats are tested for the expression of CPP by allowing them to explore both chambers and their preference are calculated.

The Effect of OLGL-Like Molecules Following Withdrawal from Cocaine.

Given the high rate of relapse among drug addicts following prolonged abstinence, exogenous administration of OLGL-like compounds is tested to show the beneficial effect during withdrawal to prevent drug relapse. Therefore, administration of OLGL-like molecules is tested to show beneficial in attenuating the expression of addictive behaviors following withdrawal. Same groups of rats as described above are assigned to these experiments. Both PS and CPP are performed as described above, but OLGL-like molecules are administered during withdrawal. The effective doses found in previous examples are used and the also the time course of treatment to determine the optimal dose and time that prevents expression of PS or CPP.

Psychomotor Sensitization (PS)

All animals are assigned to saline and cocaine treatment groups after a week of acclimation to their home cage environment. Two days before the first cocaine or saline injection, animals were habituated to the behavioral testing procedure by placement in photocell cages (Med Associates, St. Albans, Vt.) for 30 min following saline injection. On the first day of treatment (day 1), animals were habituated to photocell cages for 20 min before injection of cocaine (15 mg/kg, i.p.) or saline (1 ml/kg, i.p.). Locomotor activity (total beam breaks) was measured for an additional 30 min. For the next 4 days (days 2-5), the same procedure was applied. For ifenprodil experiments, the same procedure was applied except that ifenprodil or vehicle was i.p. injected following 20 min habituation, then cocaine or saline was injected 30 min later. Locomotion activity was measured for an additional 30 min. All rats were returned to their home cage for 21 days. On day 21 all rats were taken from their home cage and sacrificed for biochemical analysis. Criteria for sensitization were based on the coefficient of variance (CV) of the day 5/day 1 beam-break ratio in the saline group (CV=SD/mean) as previously described (Boudreau and Wolf, 2005). The CV provides a measure of variability within the saline group. A cocaine-injected rat was considered sensitized if its increase in activity over the course of cocaine treatment (day 5/day 1 beam break ratio) exceeded the CV of the saline. For this analysis, day 5/day 1 beam break ratios were calculated based on the first 30 min of activity after injection.

Conditioned Place Preference (CPP)

The CPP apparatus (Med Associates) consists of two visually distinct conditioning compartments. One contains white-colored walls and wire mesh flooring (28 cm×21 cm) while the other has black-colored walls and steel rod flooring (28 cm×21 cm). The compartments are connected by a smaller center compartment (12 cm×21 cm). Infrared beams located at the bottom of the wall allow assessment of animal preference for each compartment. CPP experiments are be carried out at predefined times of day. Following a 3-day acclimation, a biased CPP design are conducted as follows: the animals were placed in the central gray compartment for 5 min and then they are free to explore all three compartments for 15 min. The time spent in each compartment is analyzed by automated software and the results are used to determine the initial preference. The least preferred compartment for each subject is then be assigned to be the drug-paired compartment. The conditioning period is begin one day following the habituation session. Cocaine or saline injections is given each day. The animals received four saline (1 ml/kg, i.p.) and four cocaine (15 mg/kg, i.p.) injections on alternating days and are confined to the allocated compartment for a 15 min period. Thus, a total of 8 days of training is conducted. To evaluate the establishment of cocaine-induced CPP, the animals are tested one day following the last conditioning day. Each animal is placed in the central compartment for 5 min followed by a 15 min period of free access to all compartments. CPP score was defined as the percentage determined by: 100*(time spent in drug-paired chamber−time spent in saline-paired chamber)/(time spent in drug-paired chamber+time spent in saline-paired chamber).

When drugs are administered during withdrawal, the standard cocaine CPP protocol is conducted. One day after completion of conditioning to cocaine, half of the animals from each treatment group receives daily injections of drug for seven days, while the other half receives daily injections of saline. On the 7th day, the CPP test is performed as described above.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating at least one of addiction disorder, abuse disorder, withdrawal syndrome during a rehabilitation or detoxification from abusive substance addiction treatment, relapse addiction during or after rehabilitation or detoxification from abusive substance addiction treatment, including any condition and symptom associated therewith in a patient suffering therefrom, said method comprising administering to said patient a unsaturated fatty acid amide of an amino acid, including a stereoisomer and a salt thereof.

2. The method of claim 1, wherein said fatty acid moiety is selected from a a mono-unsaturated fatty acid moiety and a poly unsaturated fatty acid moiety.

3. The method of claim 1, wherein said amino acid is selected from glycine, dimethylglycine, alanine, serine, cysteine, tyrosine and phenylalanine.

4. The method of claim 1, wherein said amino acid is substituted by at least one group selected from straight or branched —$C_1$-$C_6$ alkyl, straight or branched —$C_2$-$C_6$ alkenyl, straight or branched —$C_2$-$C_6$ alkynyl, —OH, and —O($C_1$-$C_{10}$ alkyl).

5. The method of claim 1, wherein said amino acid is substituted by at least one straight or branched —$C_1$-$C_6$ alkyl.

6. The method of claim 1, wherein said fatty acid moiety is substituted by at least one group selected from —$C_1$-$C_6$ alkyl, —OH, —O($C_1$-$C_{10}$ alkyl), —SH and —S($C_1$-$C_{10}$ alkyl).

7. The method of claim 1, wherein said fatty acid moiety is substituted by at least one —$C_1$-$C_6$ alkyl.

8. The method of claim 1, wherein said fatty acid amide of an amino acid is a compound of general formula (I), including a stereoisomer and a salt thereof:

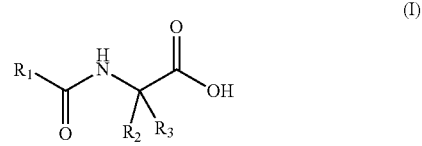

(I)

wherein
R$_1$ is selected from straight or branched —$C_{13}$-$C_{22}$ alkenyl and straight or branched —$C_{13}$-$C_{22}$ alkynyl; optionally substituted by at least one group selected from straight or branched —$C_1$-$C_6$ alkyl, —OH, —O($C_1$-$C_{10}$ alkyl), —SH and —S($C_1$-$C_{10}$ alkyl);
R$_2$ and R$_3$ are independently selected from H, straight or branched —$C_1$-$C_6$ alkyl, straight or branched —$C_2$-$C_6$ alkenyl, straight or branched —$C_2$-$C_6$ alkynyl; each optionally substituted by at least one —OH, —SH, —O($C_1$-$C_6$ alkyl), phenyl and phenol;
provided that at least one of R$_2$ and R$_3$ is different than H.

9. A method of claim 1, wherein said addiction is drug addiction, cigarette addiction, alcohol addiction, food addiction, behavioral addiction and any combinations thereof.

10. A method of claim 1, wherein said addiction is selected from nicotine addiction, opioid addiction, drug addiction, pain killer drug addiction, cocaine addiction, behavioral addiction and any combinations thereof.

11. A method of claim 1, wherein said substance is a drug, a cigarette, alcoholic beverage, food and any combinations thereof.

12. A method of claim 1, wherein said substance is selected from nicotine, opioid, cocaine, alcohol, food, pain killer drug and any combination thereof.

* * * * *